United States Patent [19]

Arold

[11] 4,130,607

[45] Dec. 19, 1978

[54] PREPARATION OF DITHIOPHOSPHORIC ACID DIESTER HALIDES

[75] Inventor: Hermann Arold, Wuppertal, Germany

[73] Assignee: Bayer Aktiengesellschaft, Leverkusen, Germany

[21] Appl. No.: 830,381

[22] Filed: Sep. 2, 1977

[30] Foreign Application Priority Data

Sep. 24, 1976 [DE] Fed. Rep. of Germany ....... 2642982

[51] Int. Cl.$^2$ .............................................. C07F 9/20
[52] U.S. Cl. ..................................... 260/973; 260/960
[58] Field of Search ................................ 260/960, 973

[56] References Cited

U.S. PATENT DOCUMENTS

| 2,897,227 | 7/1959 | Slagh | 260/973 X |
| 3,862,957 | 1/1975 | Dawes et al. | 260/308 R |
| 3,873,647 | 4/1975 | Pitt et al. | 260/973 OR |

FOREIGN PATENT DOCUMENTS

| 2327377 | 5/1973 | Fed. Rep. of Germany | 260/954 |
| 184863 | 10/1966 | U.S.S.R. | 260/960 |

OTHER PUBLICATIONS

Abstract of Japenese Patent Application J4 9086-347.

*Primary Examiner*—Anton H. Sutto
*Attorney, Agent, or Firm*—Sprung, Felfe, Horn, Lynch & Kramer

[57] ABSTRACT

A process for the preparation of a dithiophosphoric acid diester halide of the formula $$R^1S-P\begin{matrix}S\\\parallel\end{matrix}\begin{matrix}OR^2\\\diagdown\\Hal\end{matrix}$$

in which
$R^1$ and $R^2$ each independently is alkyl with 1 to 5 carbon atoms, and
Hal is halogen, comprising reacting an S-alkyl dihalide of the formula $$R^1S-P\begin{matrix}S\\\parallel\end{matrix}\begin{matrix}Hal\\\diagdown\\Hal\end{matrix}$$

with an alcohol of the formula $R^2OH$ at a temperature of about $-5°$ to $-90°$ C in the presence of about a 5 to 200% molar excess of potassium hydroxide. Advantageously about a 10 to 600% molar excess of alcohol is employed, $R^1$ is n-propyl, $R^2$ is ethyl, Hal is chlorine, and the reaction is effected in an aliphatic or aromatic optionally chlorinated hydrocarbon or an ether.

10 Claims, No Drawings

PREPARATION OF DITHIOPHOSPHORIC ACID DIESTER HALIDES

The present invention relates to an unobvious process for the preparation of certain known dithiophosphoric acid diester halides, which can be used as intermediates for the synthesis of plant protection agents (see, for example, U.S. Pat. No. 3,862,957, German Offenlegungsschrift (German Published Specification) 2,327,377 and Published Japanese Patent Application 4,986,347).

It is already known that O,S-(dialkyl-, diaryl- or monoaryl-monoalkyl) dithiophosphoric acid diester chlorides are obtained when S-(alkyl or aryl) dithiophosphoric acid ester dichlorides are reacted with alcohols or phenols in the presence of tertiary amines, namely trialkylamines, in organic solvents or without acid acceptors and without solvents (see USSR Patent Specification 184,863).

However, this process has the disadvantage that the products concerned are obtained only in very poor yields and in a very impure form, impurities to be mentioned being, above all, unreacted starting material and the dithiophosphoric acid triester. The yields are only 20 to 65% of theory. A further great disadvantage of this process is that in the case of re-use, as is indispensible in industrial processes, the organic bases used to bind the acid liberated during the reaction must be recovered, which means additional expenditure and high costs. A useful process for the industrial preparation of dithiophosphoric acid diester halides from dithiophosphoric acid ester dihalides without using organic bases has not hitherto been described in the literature.

A procedure which does not have any of these deficiencies and which gives the desired products not only in good yields but also in high purity is thus of great interest.

The present invention now provides a process for the preparation of a dithiophosphoric acid diester halide of the general formula

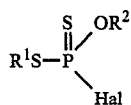

in which
R¹ and R², which may be identical or different, each represent alkyl with 1 to 5 carbon atoms, and
Hal denotes halogen, preferably chlorine, in which an S-alkyl dihalide of the general formula

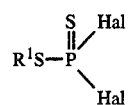

in which
R¹ and Hal have the meanings stated above, is reacted with an alcohol of the general formula

in which
R² has the meaning stated above, using about a 5 to 200% molar excess of potassium hydroxide, at a temperature of about −5° to −90° C., optionally in the presence of an organic solvent.

Preferably, R¹ represents straight-chain or branched alkyl with 1 to 5 carbon atoms, such as methyl, ethyl, n-propyl, n- sec.- or iso-butyl or n-pentyl, and R² represents straight-chain or branched alkyl with 1 to 4 carbon atoms, such as methyl, ethyl, n- or iso-propyl or n-, sec.-, iso- or tert.-butyl, but especially ethyl.

It is to be described as exceptionally surprising that under these reaction conditions the process according to the invention can proceed in such a smooth and uniform manner and can give the desired end products of the formula (I) - which hitherto could be prepared only in poor yields — in high purity and good yields, since it could not be foreseen that the reaction would proceed at a sufficient rate at the temperatures applied, or that virtually no saponification, that is to say reaction of the starting compound (II) with the potassium hydroxide to give thiophosphoric acids, would occur.

The process according to the invention has a number of advantages. Of these it may be mentioned, in particular, that the industrial feasibility is greatly simplified by the omission of the working-up again of organic bases and by the short reaction time.

Furthermore, the high purity and good yield, already mentioned above, of the products obtainable by the process according to the invention may be mentioned as being advantageous.

If S-n-propyl dithiophosphoric acid ester dichloride, ethanol and potassium hydroxide are used, for example, as the starting materials, the course of the reaction according to the process can be represented by the following equation:

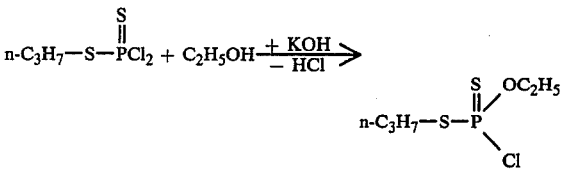

The S-alkyl dithiophosphoric acid ester dihalides (II) which are to be used as the starting materials are already known (see, for example, USSR Patent Specifications 175,962; 185,902 and 187,912).

Individual examples which may be mentioned are: S-methyl, S-ethyl, S-n-propyl, S-iso-propyl, S-n-butyl, S-iso-butyl, S-sec.-butyl, S-tert.-butyl and S-n-pentyl dithiophosphoric acid ester dichloride.

The alcohols (III) which are also to be used as starting materials are known from the literature and can also be easily prepared on an industrial scale. Individual examples of these which may be mentioned are: methanol, ethanol, propan-(1 or 2)-ol, butan-2-ol and 2-methylpropan-1-ol.

The process according to the invention is appropriately carried out using a suitable solvent or diluent. Virtually all inert organic solvents may be used, especially aliphatic and aromatic, optionally chlorinated hydrocarbons, such as benzene, toluene, xylene, benzine, methylene chloride, chloroform, carbon tetrachloride and chlorobenzene, or ethers, for example diethyl ether, dibutyl ether and dioxane.

The reaction temperature can be varied within a wide range. In general, the reaction is carried out at from −5° to −90° C., preferably at about −50° to −70° C., and especially at about −30° to −65° C.

In general, the reaction is allowed to proceed under normal pressure. For carrying out the process according to the invention, the alcohol and the base can be employed in excess. Appropriately, the relevant dithiophosphoric acid ester dihalide is initially introduced in one of the solvents indicated above and reacted at $-50°$ to 90° C., preferably using about a 10–600% molar excess of alcohol. The alcohols to be used according to the invention can contain up to about an equimolar amount of water without the course of the reaction being adversely influenced.

In order to complete the reaction, the mixture is subsequently further stirred for some time, usually about one hour to 6 hours at the temperatures indicated above, preferably at about $-5°$ to $-50°$ C. Thereafter, aqueous hydrochloric acid solution is added to the mixture at about $-10°$ to $-25°$ C. and the phases are separated. The organic phase is worked up in the customary manner by washing, drying and distilling off the solvent.

The short reaction times enable the process also to be carried out continuously according to a particular embodiment. This procedure is useful, in particular, when fairly large batches are made, since the volume of the reactor can be kept relatively small, which is advantageous at the reaction temperatures according to the invention. Subsequent reaction, washing with hydrochloric acid, phase separation and removal of the solvent can then be carried out continuously or discontinuously.

In most cases, the products are colorless to pale yellow-colored liquids, which can be identified and characterized by their refractive index and gas chromatography.

As already mentioned above, the dithiophosphoric acid diester halides which can be prepared according to the process can be used as intermediates for syntheses of insecticidal and acaricidal active compounds.

The preparative examples which follow illustrate the process according to the invention:

EXAMPLE 1

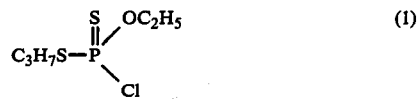

A solution of 78.3 g (1.4 mol) of potassium hydroxide in 220 g of 96% strength ethanol was added to a mixture of 209 g (1 mol) of S-n-propyl dithiophosphoric acid ester dichloride in 330 ml of wash benzine, of boiling range 100°–140° C., at an internal temperature of $-65°$ to $-70°$ C. in the course of 1 hour, while stirring and cooling externally, and the mixture was stirred for 2.5 hours at $-35°$ C. In order to work up the reaction mixture, 10% strength hydrochloric acid was added, while cooling externally and stirring and starting at an internal temperature of $-30°$ C., until a pH value of less than 4 was reached and the potassium chloride had dissolved. The internal temperature after the hydrochloric acid addition was 0° to $-5°$ C. After separating off the aqueous layer, the solvent was stripped off under reduced pressure at a maximum temperature of 60° C.

The pale yellowish, liquid residue (210 g) contained, according to gas chromatography, 93% of S-n-propyl O-ethyl dithiophosphoric acid diester chloride, 1.5% of S-n-propyl dithiophosphoric acid ester dichloride and 1.9% of S-n-propyl O,O-diethyl dithiophosphoric acid triester. The net yield was 89% of theory.

The table which follows contains further examples and gives the essential reaction conditions:

Table

Examples of the reaction according to the equation $$R^1S-\overset{S}{\underset{Cl}{\overset{\|}{P}}}\diagdown_{Cl} + R^2OH + KOH \longrightarrow R^1S-\overset{S}{\underset{Cl}{\overset{\|}{P}}}\diagdown_{Cl}^{OR^2} + KCl + H_2O$$

(II)    (III)    (I)

| Example No. | Starting materials and amounts employed | | | | KOH mol | Solvent | Temperature during addition (° C) | Subsequent stirring time at $-20°$ C (hours) | Yield of (I) [g] |
|---|---|---|---|---|---|---|---|---|---|
| | (II) R¹ | mol | (III) R² | mol | | | | | |
| 2 | CH₃ | 0.1 | C₂H₅— | 0.25 | 0.14 | 30 ml of wash benzine | $-70$ | 4 | 17 |
| 3 | C₂H₅— | 0.1 | C₂H₅— | 0.25 | 0.2 | 30 ml of wash benzine | $-70$ | 6 | 14.2 |
| 4 | n-C₃H₇— | 1 | C₂H₅— | 4.8 | 1.4 | 400 ml of wash benzine | $-70$ | 2 | 215 |
| 5 | n-C₃H₇— | 0.5 | n-C₃H₇— | 5 | 0.8 | 300 ml of wash benzine | $-70$ | 4 | 100 |
| 6 | n-C₃H₇— | 0.5 | n-C₄H₉— | 4 | 0.8 | 300 ml of wash benzine | $-70$ | 4 | 121.5 |
| 7 | n-C₄H₉— | 0.1 | C₂H₅— | 0.25 | 0.2 | 30 ml of wash benzine | $-70$ | 6 | 17.5 |

It will be appreciated that the instant specification and examples are set forth by way of illustration and not limitation, and that various modifications and changes may be made without departing from the spirit and scope of the present invention.

What is claimed is:

1. A process for the preparation of a dithiophosphoric acid diester halide of the formula

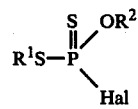

in which $R^1$ and $R^2$ each independently is alkyl with 1 to 5 carbon atoms, and Hal is halogen, comprising reacting an S-alkyl dihalide of the formula

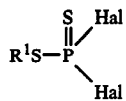

with an alcohol of the formula $R^2OH$ at a temperature of about −5° to −90° C. in the presence of about a 5 to 200% molar excess of potassium hydroxide.

2. A process according to claim 1, in which the reaction is carried out at about −50° to −70° C.

3. A process according to claim 2, in which the reaction is carried out at about −30° to −65° C.

4. A process according to claim 1, in which about a 10 to 600% molar excess of alcohol is employed.

5. A process according to claim 1, in which $R^1$ is methyl, ethyl, n-propyl, n-, sec.- or iso-butyl or n-pentyl, and $R^2$ represents alkyl with 1 to 4 carbon atoms.

6. A process according to claim 5, in which $R^1$ is n-propyl and $R^2$ is ethyl.

7. A process according to claim 1, in which Hal is chlorine.

8. A process according to claim 1, in which the reaction is effected in an inert organic solvent.

9. A process according to claim 8, in which the solvent is an aliphatic or aromatic optionally chlorinated hydrocarbon or an ether.

10. A process according to claim 4, in which about a 10 to 600% molar excess of alcohol is employed, $R^1$ is n-propyl, $R^2$ is ethyl, Hal is chlorine, and the reaction is effected in an aliphatic or aromatic optionally chlorinated hydrocarbon or an ether.

* * * * *